United States Patent [19]

Constant et al.

[11] Patent Number: 5,542,004
[45] Date of Patent: Jul. 30, 1996

[54] FOAM ANALYZING METHOD AND APPARATUS

[75] Inventors: Marc D. Constant, Germantown, Wis.; Albert T. Grzybowski, Mundelein, Ill.; Farhad Moalem, Bridgeport, Conn.

[73] Assignee: Miller Brewing Company, Milwaukee, Wis.

[21] Appl. No.: 797,619

[22] Filed: Nov. 25, 1991

[51] Int. Cl.$^6$ .................................................. G06K 9/00
[52] U.S. Cl. .......................... 382/141; 382/142; 382/100
[58] Field of Search .............................. 382/1, 8, 25, 48; 358/101, 106, 107; 356/379, 383, 384; G06K 9/00, 9/46, 9/20; H04N 7/00, 7/18; G01B 11/28, 11/06, 11/02, 11/08

[56] References Cited

U.S. PATENT DOCUMENTS

| | | | |
|---|---|---|---|
| 4,324,557 | 4/1982 | Wegstedt | 23/232 R |
| 4,628,465 | 12/1986 | Ito et al. | 382/52 |
| 4,916,640 | 4/1990 | Gasperi et al. | 364/521 |
| 4,965,841 | 10/1990 | Kaneko et al. | 382/25 |

OTHER PUBLICATIONS

Paper entitled "Experiences With the Foam Stability Analyzer, System Carlsberg" presented at the M.B.A.A. Meeting in Toronto, Canada.
Paper by J. Savel et al. entitled "A Rapid Method For Measuring the Foaming Capacity of Beer," 1989.
Article entitled "Experiences With a New Foam Stability Analyzer, System Carlsberg."An article entitled "Use of Magnetic Resonance Imaging for Evaluation of Beer Foam Characteristics," copyright 1990 by the American Society of Brewing Chemists, Inc.

Primary Examiner—Jose L. Couso
Attorney, Agent, or Firm—Quarles & Brady

[57] ABSTRACT

A method of analyzing the visually perceptible characteristics of foamable liquid, such as beer, comprises pouring a known quantity of the foamable liquid from a storage container into a clear beaker. A camera produces a video image of the beaker and its liquid and foam contents. A series of such image are periodically acquired over a definite time period. The images are electronically analyzed to derive numerical value indicating the different characteristics. A system for performing the method also is described.

13 Claims, 1 Drawing Sheet

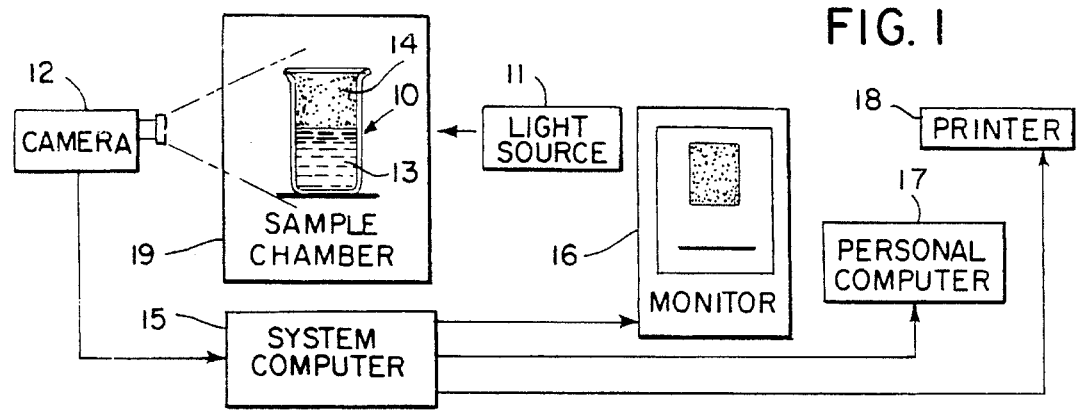
FIG. 1
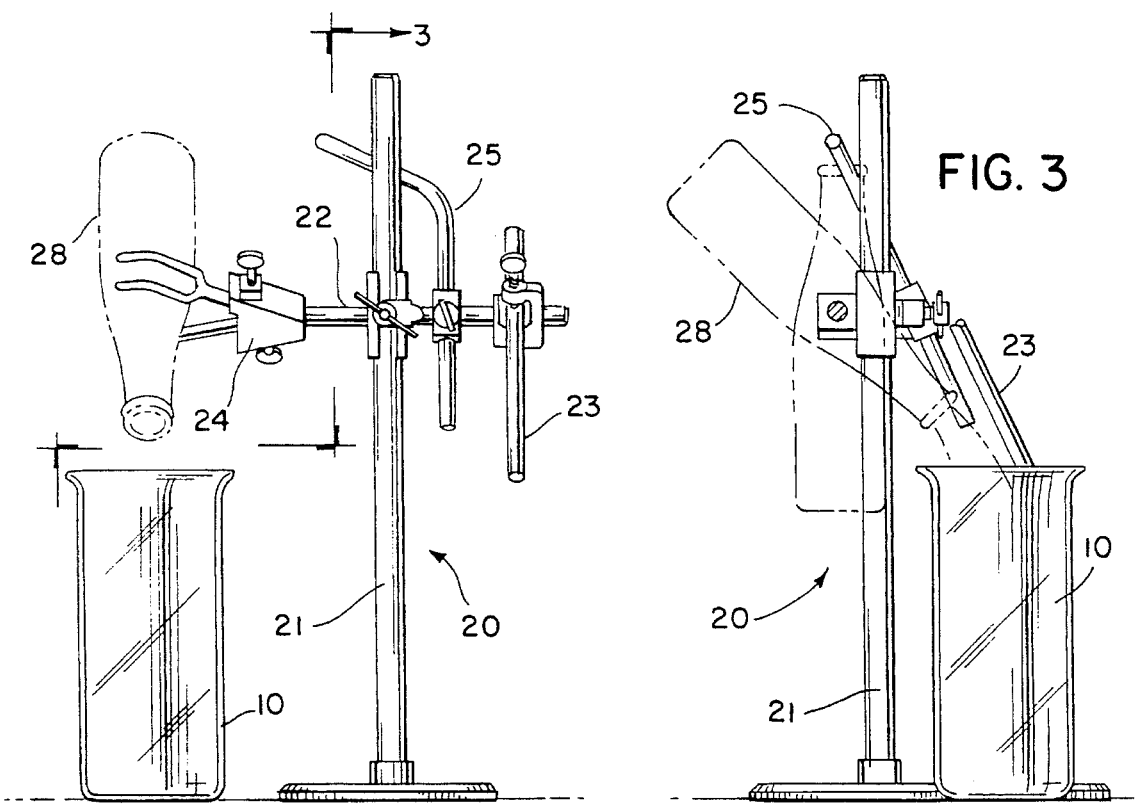
FIG. 2
FIG. 3
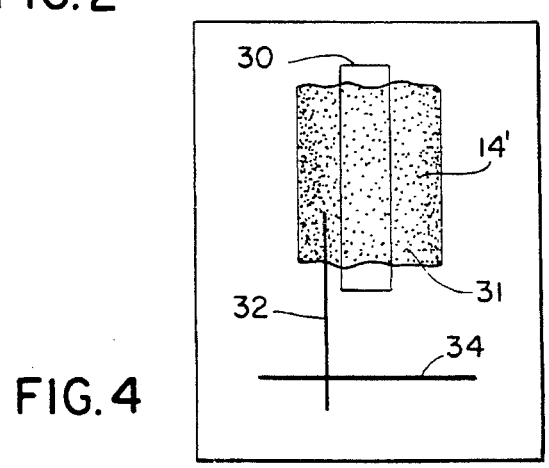
FIG. 4

FOAM ANALYZING METHOD AND APPARATUS

FIELD OF THE INVENTION

The present invention relates to a method of analyzing the visually perceptible characteristics of the foam which forms when a foamable liquid, such as beer, is poured into a container. It also relates to an apparatus for use in performing that method.

BACKGROUND OF THE INVENTION

An attractive, stable head of foam is considered an important quality factor for beer by many consumers. Therefore, brewers routinely analyze the foam characteristics of their beer as part of the quality control of the product.

The principal aim of foam analysis is to measure what customers will notice when they pour the beer. The visually perceptible properties of foam quality include the height of the foam or head formation, the stability of the foam, the foam texture or bubble size, the lacing of the foam and foam adhesion.

It has been found that the size of the foam head is largely dependent on the gas content of the beer. However, the length of head retention, or life, and the clinging of the foam to the walls of the container can be affected by minor foam and surface active constituents and the presence or absence of foaming factors which are derived from brewing ingredients and processing steps.

Various methods and apparatus are commercially available for measuring the foam characteristics of beer. However, the most popular techniques use special foam making equipment and do not recommend forming the foam as the customer would, by simply pouring the beer from a bottle or can into a clear measurement container. Commonly used methods bubble carbon dioxide through the liquid beer or sonicate the liquid using ultra sound to excite the beer and produce foam. Another technique ejects liquid beer through a special nozzle.

Once the foam was created different approaches have been used to measure the height of the liquid and/or foam. The simplest generates the foam in a graduated vessel and a technician takes measurements by eye. Automatic systems have been devised which use conductivity or optical sensors to detect the foam height. For example, one system moves a line scan camera up and down a clear container to detect the levels of the liquid and foam therein. However, the methods may not accurately sense the amount of the foam by merely detecting its height. When the foam boundary is uneven, it is difficult to get a good measurement of the foam layer by simply sensing the height at one point.

Evidence that nine of the commercially available methods or apparatus is completely satisfactory can be found in the continued efforts to measure foam stability, in some cases using exotic new equipment. For example, in an article in the *American Society Brewing Chemists Journal*, Volume 48, No. 4, 1990, Pages 139–122, a method of evaluating beer foam characteristics using magnetic resonance imaging (MRI) is described. The method depends upon the paramagnetic properties of neutrons and protons of some of the atomic nuclei present. In the technique, the beer sample is poured gently down the side of a tube and then sonicated to form a foam which is analyzed using MRI.

The described prior art methods make the foam very differently than the way beer is consumed and measure the foam characteristics indirectly. There is a need for a method and apparatus which makes the foam in the same manner as a consumer and which directly evaluates the visually perceptible properties of a foam.

SUMMARY OF THE INVENTION

It is an object of the present invention to disclose a method and system for making a foam in the same manner as the consumer and directly evaluating the visually perceptible characteristics of the foam.

The preferred method of the present invention begins by pouring a foamable liquid, such as beer, from a can or bottle at a predetermined height and angle into a transparent container, preferably of glass, which is free of foam affecting contaminants. However, other techniques for generating foam can he used with the novel video inspection system.

The transparent container with its liquid and foam contents is positioned between a light source and a stationary video camera. Video images of the container, liquid and foam are acquired periodically over a predetermined time period and analyzed electronically to create numerical values corresponding to the visually perceptible characteristics of the foam. The values are printed to form a storable record.

The foaming technique of the present invention is much simpler than the primer art systems which have been described. It basically comprises a foamable liquid pouring apparatus and video imaging system. A computerized apparatus is provided to electronically analyze the image from the video camera and generate numerical data quantifying the visually perceptible characteristics of the foam.

The present invention provides several obvious advantages over the previously described prior art methods and systems. It more accurately duplicates how the foam is produced by the consumer under normal conditions of use. In addition, it directly and faithfully views and measures the visually perceptible foam characteristics as seen by the consumer.

It will be apparent to those skilled in the art that the foregoing and additional objects and advantages can be achieved by practice of the present invention.

BRIEF DESCRIPTION OF THE DRAWINGS

FIG. 1 is a schematic view showing the video imaging and analyzing portion of the system of the present invention;

FIG. 2 is a plane view of the preferred apparatus for pouring a commercial container of foamable liquid into a clear beaker to generate foam;

FIG. 3 is a view taken along line 3—3 of FIG. 2; and

FIG. 4 depicts a binary video image produced on a monitor shown in FIG. 1.

DETAILED DESCRIPTION OF THE INVENTION

In the preferred embodiment of the present invention seen in FIG. 1, the foamable liquid, such as beer, for which the foam is to be analyzed is in a clear cylindrical beaker 10 positioned between a light source 11 and a monochrome video camera 12. For example, a one liter Berzelius beaker having a height of about 18.5 cm and an outer diameter of about 9 cm can be used. The beaker 10 is positioned so that the camera 12 can generate two dimensional video images of the beaker 10, including its liquid 13 and foam contents 14. The light source uniformly illuminates the beaker and its contents. The camera 12 remains stationary at a fixed distance with respect to the beaker 10. Such fixed positioning permits uniform measurement of different samples of foamable liquid.

The signals generated by camera 12 are transmitted to a system computer 15, such as an Allen-Bradley Company, Inc. 1771 series programmable controller that includes a Bulletin 2803 Vision Input Module and a BASIC program module. A controller of this type is described in U.S. Pat. No. 4,916,640. The system computer 15 converts the analog image signal from video camera 12 into a plurality of digital, gray scale picture elements which are further transformed for analysis into two binary images having only pure black and pure white picture elements. Different sensing regions are defined in each binary image by the system controller 15 and the number of black or white picture elements within each sensing region are counted to provide an analysis of features in the image. The specific use of such analysis with respect to the present invention will be described.

The numerical counts of the black and white picture elements within each sensing region can be displayed on a monitor 16 along with one of the binary video images. The picture element counts are transferred to the internal BASIC program module in the programmable controller 15 and used to determine the foam characteristics. At the conclusion of the test, the analysis results may be transmitted digitally to a personal computer 17 for further analysis and to a printer 18.

The preferred type of apparatus 21 for generating foam for analysis can be seen in FIGS. 2 and 3. This apparatus 20 enables the foamable liquid to be poured from a container 28 at a predetermined height and at a set angle into the beaker 10. The foam generating technique duplicates the manner in which a consumer typically pours a glass of beer. This structure insures uniformity in pouring and foam generation so that different samples of liquid can be compared.

The apparatus 20 includes cross rod 22 pivotally attached to a stand 21. A lever 23 rigidly extends perpendicularly from the cross rod 22 near one end. A standard flask clamp 24 is coupled to the other end of the cross rod 22 to grasp the container 28 holding the foamable liquid. A stop rod 25 is attached to the cross bar 22 at an orientation such that it strikes the stand 21 when the apparatus 20 is in the pouring position illustrated in the drawings.

To conduct an analysis, the height of the cross rod 22 is adjusted so that in the pouring position a predefined gap (e.g. 3.8 cm) exists between the mouth of the container 28 and the top of the beaker 10. An open container 28 holding a known quantity of the foamable liquid is placed upright within the flask clamp 24. For example, a standard twelve ounce bottle of beer is placed within the clamp, although other size bottles or cans may be used. Thereafter liquid is poured from the container 28 into the glass beaker 10 and the system computer 15 is triggered by the operator to commence the analysis. The beaker 10 containing the liquid and foam is transferred to the sample chamber 19.

An internal timer is started when the controller 15 is triggered upon liquid being poured into the beaker 10. After one minute has elapsed, the system computer 15 acquires a first video image from camera 12. The vision input module in the system computer 15 digitizes the signal from the camera and converts the gray scale image into a pair of binary images. For each conversion, all digital picture elements with a value below a user selectable threshold are set to a pure white value. The thresholds for the each binary images are chosen independently so that the picture elements for the foam will be converted to black, while all other picture elements, including those representing the liquid 13, will be white.

FIG. 4 represents a binary images being displayed on monitor 16. Due to the binarization threshold selected, the image is entirely white except for a rectangular area 14' which corresponds to the foam in the beaker 10. The vision input module of system computer 15 has been configured with a rectangular sensing region 30 enclosing approximately the middle third of the foam portion 14' in one binary image. This sensing region 30 extends above the height of the foam and below the line of the foam-liquid interface 31. A linear sensing region 32 also is defined within the other binary image produced by the vision input module and extends from below the bottom of the beaker 10 upward through the liquid into the foam 14' in the image. The white picture elements along the linear sensing region 32 correspond to the liquid 13 within the beaker 10 and are counted to provide a measurement of the height of that liquid. The particular vision input module used allows different binary images to be generated for each sensing region using separate thresholds. This permits accurate definition of the features detected by each sensing region. For simplicity of illustration, both sensing regions 30 and 32 are shown superimposed on the same binary image being displayed by monitor 16. As the camera 12 is at a fixed position relative to the beaker 10, the sensing regions 30 and 32 remain in the same relative locations in images for different samples of foamable liquid.

The system computer 15 analyzes the image by counting the number of dark and light picture elements in the sensing regions 30 and 32. For the linear sensing region 32 the number of white picture elements between the black blobs for the foam 14' and base 34 for the beaker 10 are counted as a measurement of liquid height. These picture element counts are stored temporarily as representing the state of the liquid and foam at the one minute interval. The one minute delay before acquiring the first video image provides a sufficiently long interval for the foam-liquid interface to be well defined. Other video images are acquired and similarly processed at thirty second intervals until five minutes have elapsed from the pouring of the liquid into the beaker 10. The image acquisition phase then is suspended. At that point in time, nine sets of picture element counts from the two sensing regions 30 and 32 have been stored in a table within memory of the programmable controller 15.

The total liquid poured into the beaker 10 is determined by a final measurement taken by counting white picture elements between the black blobs in sensing region 32 at least fifteen minutes after the liquid was poured. Typically a slight amount of foam remains at this time to produce a black blob in the linear sensing region 32. If this is not the case, the beer in the beaker 10 is sonicated until a small blob appears in the image. After the final measurement is taken, the acquired data is transferred to the BASIC program module in the system computer 15 where the data is used to determine specified attributes of the foam.

The BASIC program module of the system computer 15 calculates the density of the foam by determining the amount of the original foamable liquid that was converted to foam one minute after pouring. The volume of liquid 13 within the beaker 10 at the one minute interval is proportional to the height of the liquid as indicated by the first white picture element count for sensing region 32 and the dimensions of the beaker 10. Thus, the liquid content of the foam 14 at the one minute interval can be represented by the BASIC program module subtracting the height of liquid 13 in the beaker at that time from the height of liquid in the final measurement. As the beaker 10 has a uniform inner diameter, the height of the liquid and foam are directly proportional to volume. If preferred, the height measurement and the inner diameter of the beaker can be used to compute the actual volumes.

The system computer 15 also derives the amount of foam present at each of the sampling times based upon the number of black picture elements counted within sensing region 30 in each image acquired from camera 12. The BASIC program module uses these counts and the thirty second sampling interval to calculate the rate at which the foam 14 collapses. The density, height, volume and rate of collapse of the foam 14 are numerical data representing visual characteristics of the foamable liquid and are printed by printer 18.

The measurements for a given sample of beer can be transferred from the system computer 15 to the personal computer 17 for further analysis. For example, the data for several samples can be compared and statistically analyzed by the personal computer.

In addition to being especially useful as a quality control tool for brewer's own beer, the method and system of the present invention also can be used to evaluate and compare competing brands of beer or beer made by different brewing processes or from different ingredients. The system of the present invention also is unique in that it utilizes commercially available components.

It will be apparent to those skilled in the art, that a number of changes and modifications can be made without departing from the spirit and scope of the present invention. For example, other techniques may be employed to generate foam for analysis by the present video inspection system. In addition, the acquired measurement data can be used to calculate other characteristics of the foam. Therefore, it is intended that the invention only be limited by the claims.

We claim:

1. A method of analyzing visually perceptible characteristics of foam which is formed when a foamable liquid is poured, said method comprising:

(a) pouring the foamable liquid from a predetermined height at a set angle into a transparent container to generate a foam;

(b) generating a series of two-dimensional video images of the container, as well as any liquid and foam within the container;

(c) electronically analyzing the video images to derive numerical values quantifying the visually perceptible characteristics of the foam by defining a two-dimensional region in a video image and counting picture elements within the region that correspond to foam.

2. The method as recited in claim 1 wherein said step of electronically analyzing further comprises measuring an amount of the foamable liquid that was converted to foam at a predefined interval after the pouring step.

3. The method as recited in claim 1 wherein said step of electronically analyzing further comprises determining how much liquid is present in different generated video images.

4. The method as recited in claim 1 wherein said step of electronically analyzing further comprises determining from the video image a rate at which the generated foam collapses.

5. The method as recited in claim 1 wherein said step of electronically analyzing further comprises counting picture elements within a predefined region of the video image to determine a height characteristic of liquid in the container.

6. A system which analyzes visually perceptible characteristics of foam produced from a foamable liquid, said system comprising:

a transparent vessel;

means for generating foam within said vessel;

a camera for generating a plurality of two-dimensional video images of the vessel, as well as any liquid and foam within the vessel; and means for electronically analyzing the video images generated by said camera, and having a first mechanism which defines a two-dimensional region in a video image and counts picture elements within the region that correspond to foam.

7. The system as recited in claim 6 wherein said means for electronically analyzing further comprises a second mechanism which counts picture elements within a predefined region of a video image to determine a height characteristic of liquid in the vessel.

8. The system as recited in claim 6 wherein said means for electronically analyzing comprises means for comparing picture element counts received from said first mechanism to determine a rate of collapse of foam within said vessel.

9. The system recited in claim 7 wherein said means for electronically analyzing calculates foam density in response to picture element counts from said first and second mechanisms.

10. The system of claim 6 wherein said means for electronically analyzing includes an apparatus for counting picture elements in the video signals which represent liquid in the video image.

11. A system for automatically analyzing visually perceptible characteristics of foam from a foamable liquid, said system comprising:

a transparent vessel for receiving a poured foamable liquid;

means for pouring, a foamable liquid from a storage container from a predetermined height at a set angle into said vessel to form a foam;

a camera for generating video signals representing a video image of foam and liquid in the vessel;

means for analyzing video images by periodically acquiring a video image from said camera, defining first and second regions in the video image, and counting picture elements within the first and second regions; and means for deriving data regarding the visually perceptible characteristics from counts of picture elements received from said means for analyzing video images.

12. The system as recited in claim 11 wherein said means for deriving data calculates a rate of foam collapse from the counts of picture elements.

13. The system as recited in claim 11 wherein said means for deriving data calculates foam density from counts of picture elements.

* * * * *